(12) United States Patent
Sharp

(10) Patent No.: US 6,194,007 B1
(45) Date of Patent: *Feb. 27, 2001

(54) RODENT CONTROL

(75) Inventor: Thomas Sharp, Amarillo, TX (US)

(73) Assignee: Mitchell Arnold, Odessa, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 11 days.

(21) Appl. No.: 09/215,885

(22) Filed: Dec. 19, 1998

(51) Int. Cl.⁷ ............... A01N 25/08; A01N 25/34; A01N 59/00; A01N 6/25; A01M 25/00
(52) U.S. Cl. .............. 424/657; 424/84; 424/405; 424/439; 424/442; 424/489; 424/658; 424/659; 424/660; 424/682; 424/684; 424/688; 424/691; 424/692; 424/724; 514/951; 43/124; 43/131
(58) Field of Search .................. 424/405, 724, 424/657–660, 688, 691, 692, 84, 439, 442, 489, 682, 684; 43/124, 131; 514/951

(56) References Cited

U.S. PATENT DOCUMENTS

| 4,379,139 | * | 4/1983 | Dawson | 424/84 |
| 4,505,541 | * | 3/1985 | Considine et al. | 385/107 |
| 5,596,834 | * | 1/1997 | Ritter | 43/124 |

* cited by examiner

*Primary Examiner*—John Pak
(74) *Attorney, Agent, or Firm*—Christopher Whewell

(57) ABSTRACT

Disclosed herein are compositions which are highly effective rodenticides. The compositions include a plurality of glass whiskers which rodents are naturally attracted to for purposes of nest building, or are otherwise induced to pick up in their mouths. Upon biting the whiskers for either transport or eating, the rodents oral mucosa becomes irritated, often to the extent that the rodents are unable to subsequently eat without excruciating pain. Hence, the rodents death by starvation is inevitable.

17 Claims, No Drawings

RODENT CONTROL

The present invention relates to a method for rodent control, as well as compositions useful in the method.

The presence of rodents near areas of human habitation has been considered a nuisance for quite some time. Generally speaking, rodents are scavenging mammals which forage areas in search of foodstuffs which may comprise garbage and materials which are generally considered inedible by human standards. It is a fact that rodents are carriers of various diseases themselves which are readily communicated to other mammalian species, including man, by direct contact including bites and indirectly by airborne dusts containing particulants derived from rodent feces, saliva, and urine which are known to contain a myriad of pathogens including Hantavirus, Salmonellosis, Pasteurellosis, Leptospirosis, Swine Dysentary, Trichinosis, and Toxoplasmosis. It is believed by many authorities that the Bubonic plague of Europe during the middle ages had rodents as its primary means of transmittal. Today, rodents continue to play this same role of carrier.

Rodents also cause a wide variety of physical damage to human interests, particularly in farm areas. Since rats produce 25,000 droppings per year and mice produce 17,000 droppings per year, contaminated animal feeds are common. Additionally, during their forage for food and nesting materials, rodents cause structural damage to wood and wiring. It has been estimated that a single rat will eat, spoil, or damage $25 worth of grain per year.

Rodents have an enormous breeding potential. It has also been estimated that a single pair of rats and their offspring are capable, under ideal conditions, of producing 20,000,000 young in just three years, while mice reproduce even faster. This breeding potential, combined with the damage potential make it apparent that the presence of just a few rodents can lead to significant damages, in addition to the various health risks.

Accordingly, various methods for control of rodents have been devised over the centuries, particularly for areas in which human population density is high such as in large cities. Of the various means employed in rodent control, perhaps the most widely practiced are those which relate to mechanical traps designed to entrap or kill various rodents and to poisonous chemical substances which are either intended for rodent ingestion or as a deterrent to the rodents owing to the offensiveness of the chemicals. The prior art is replete with both types of rodent control. U.S. Pat. Nos. 3,223,231; 3,764,693; 3,816,610; 3,867,546; 3,929,983; 4,035,505; 4,156,714; 4,287,183; 4,520,007; 4,783,481; 4,952,401; 4,992,275; 5,044,113; and 5,720,951, the entire contents of which all are herein incorporated by reference, are but a few prior art patents which are concerned with rodent control.

However, it has been observed in many cases that rodents, owing undoubtedly to their resilience developed through breeding under a wide range of stressful conditions, are quick to develop an increased tolerance for chemical substances that were initially effective as rodenticides. Although the tolerance level developed is dependent upon the quantity and type of rodenticide, the result of increased tolerance is always observed. It is to this factor that the ultimate ineffectiveness of nearly all rodenticides, whether passive or active, can be attributed.

As far as mechanical traps designed to catch or kill rodents are concerned, such contrivances are design-limited to a pre-determined number of possible rodents against which they are effective. In other words, one rodent trap can only catch or kill one rodent at a time without having to be re-set by a human operator. Since rodents tend to breed at high rates, rodent traps are generally ineffective against controlling even modest populations of these animals without constant human maintenance of the traps, with the human presence complicating matters by frightening away the rats to be trapped.

It is apparent from the foregoing drawbacks associated with known means for rodent control that if effective control of rodent populations is ever to be achieved, particularly in areas where rodent population density is high, a means for killing rodents will have to be developed to which the rodents can neither develop an increased resistance, which is not physically limited by design to only being able to catch or kill one rodent at a time, and in which the rodents are not frightened by the constant presence of human beings. The present invention sets forth a new method by which these criteria can be achieved, as well as compositions of matter useful therefor.

SUMMARY OF THE INVENTION

It is a fact that in addition to foraging for food, rodents engage in reproductive behavior and nesting activities. The instinct to build nests is inseparably tied in with the reproductive activity of these pests. Whenever a rodent is to have offspring, there will in nearly all cases be a nest.

Rodents have poor eyesight but excellent senses of smell, taste, touch, and hearing. They do not like open areas, and prefer contact with walls and other objects. They do not range far from their nests, with the maximum range for rats being 45 meters and that for mice being 9 meters. Rats are extremely apprehensive about new objects and will avoid them for several days, while mice quickly accept new objects. Both are good climbers. The favorite food of mice is grain, while rats prefer fresh meat and grains. Both prefer to eat and drink every day, but mice can survive several days without water.

The above description is provided to provide the reader an understanding of the importance of conditions under which rodents normally prefer to flourish, and is indicative of preferable nesting conditions. Rodent nests have been found to be constructed of various materials and may be found in various locations provided the above requisites are present.

In general, rodent nesting materials have been found to comprise straw, hay, cloth, cotton, newspaper, cardboard, wood shavings, soft fiberglass insulation, animal hair, or any fibrous material which is soft to the touch and fluffy. It is seen that nearly all materials from which rodent nests are constructed are both absorbent and insulating. It is believed such materials are instinctively preferred, inter alia, in order to keep the young warm.

The present invention comprises placing a special stiff form of glass fibers, ("whiskers") somewhat reminiscent of cat whiskers, in a vicinity where rodents are known to be populous. The fibrous glass material is perceived by the rodents as being a well-suited nesting material. In order to move the stiff fibrous glass material from its initial location to the nesting site, the rodents use their mouths as a means of holding the stiff whiskers in a secured position for transport. The stiff whiskers are easily fragmented, however, and microscopic slivers of the whiskers fracture and penetrate the inside portions of the rodent's mouths. A local swelling occurs around each site of entry of the slivers of the stiff glass whiskers. This swelling provides irritation to the rodents mucosa to the extent that the rodents find it impossible to eat without encountering unbearable, excruciating pain. Death from starvation ensues in short order. Additionally, it has been observed that when the instant invention is employed as a rodenticide composition and procedure, the rodents generally return to their nests to die; thus the area of infestation is not littered with the carcasses of the dead animals.

Glass has been known for centuries. For purposes of the instant specification and the appended claims, glass may be classified as an amorphous material of varied composition. Commercial glasses may be divided into the soda-lime-silica glasses and special glasses, with over 95% of the tonnage produced belonging to the former class. Such glasses are made from three minerals—silicon dioxide, calcium carbonate, and sodium carbonate.

Fused silica itself is an excellent glass; however, such is rarely used in the pure form as its melting point is above about 1700 degrees centigrade and such high temperatures are expensive to reach and maintain. In order to reduce the melting point of fused silica, various additives or fluxes may be added to the melt. By adding about 25% of sodium carbonate to the melt, the melting point is reduced to just 850 degrees centigrade, thus considerably reducing the difficulty of melting.

Other additives may be substituted in the place of, (either alone or in combination with other materials), or used in conjunction with sodium carbonate. Suitable other materials include magnesium oxide, aluminum oxide, rare earth oxides, boron oxides, lead oxide, or virtually any metallic oxide which imparts desired properties to the melt for purposes of either enhanced processibility during manufacture of the glass or enhanced physical properties of the finished products themselves. For purposes of the instant invention, the word glass means a liquid that has the property of cooling below its freezing point without crystallizing, thus becoming a liquid of increasingly high viscosity until it is so stiff that by all ordinary definitions it has the properties of a solid, wherein said liquid contains at least 35% by weight of silicon dioxide.

Thin strands of glass have been known for centuries, and threads of glass were wound around vessels as a decoration in ancient Egypt. In 1938 a new glass fiber was produced by the Owens-Illinois Glass Company working in conjunction with the Corning Glass Works (Ownes-Corning). The method developed by G. Slayter and J. Thomas passed molten glass from a glass-tank forehearth to a bushing of noble metal having a number of orifices in its base through which fine streams of glass drained downward. The streams passed between two mutually-converging, downwardly-directed, high-pressure jets of air or steam. The strands are attenuated by the turbulent high-velocity gases to much finer fibers (0.00035–0.00080 in.) than were available previously. The mass of fleecy material so produced is caused to pass through a spray of thermosetting binder, and is caught on a conveyor belt and is compressed to a desired density. The binder is set by baking, and the finished material is formed into blocks, blankets, boards, insulation, refractories, and cements. Processes for producing glass fibers or strands are well-known to those skilled in the art. Such processes include, but are by no means limited to those described in U.S. Pat. Nos. 4,285,712; 4,146,375; 4,178,162; 4,167,403; 4,149,865; 3,649,231; 3,573,016; 3,429,972; 3,358,066; 3,332,758; 3,328,144; 3,321,290; 3,280,967; 3,264,076; 3,261,677; and 2,465,283, the entire contents of all of the foregoing being incorporated herein by reference.

DETAILED DESCRIPTION OF THE PREFERRED EMBODIMENTS

The present invention provides a method and composition of matter useful for killing rodents and other pests.

Glass fibers must normally be soft and pliable, in order to be useful in various employments. For purposes of the instant invention, the glass fibers are more properly classifiable as whiskers, which must be stiff. Linear fibers which are soft and pliable may be held in the hands and bent 180 degrees without breaking, and may often even be tied into knots. Linear stiff glass whiskers, useful in this invention, on the other hand, generally break in two when bent beyond about 45 degrees.

The primary factor which determines whether a given glass fiber is pliable or stiff is the thickness of the fiber, given a given composition. Typically, pliable fibers have diameters less than about 0.002 inches in diameter. The whiskers of this invention are substantially round in cross section comprise glass, and have diameters in the range of about 0.0025 inches to about 0.0100 inches. More preferably, the whiskers hereof have diameters in the range of 0.00375 inches to 0.00625 inches. Still more preferably, the range is between about 0.0045 and 0.0058 inches, with a thickness of 0.005375 inches being most preferable.

The length of the whiskers employed as rodenticide herein is not critical to the way in which the fibers function. However, to maximize the effectiveness of the stiff whiskers, they must be appealing to the rodents that believe them to be suitable nesting materials. For killing rats, the preferred length of the whiskers is between about 0.10 inches and 6.0 inches, including any and all lengths therebetween, with a length between 0.5 and 3.0 inches being more preferably, and a length of 2.0 inches being the most preferred. However, a mixture of different whisker lengths in this range is useful herein. For killing mice, the preferred length is between about 0.10 and 3.0 inches, including any and all lengths therebetween, with a length between 0.25 and 2.00 inches being more preferable, and with 1.5 inches being most preferable. Again, a mixture of different whisker lengths in this range is useful herein.

The exact composition of the whiskers is not critical to their functioning as taught herein. All that is necessary is that the whiskers be appealing enough to the targeted rodents for them to put the whiskers in their mouths. For this purpose, the whiskers may be long enough in length to appear desirable for use as nesting materials from the rodents' perspective, or very short whiskers, such as those produced by grinding long whiskers into a powder of 10-mesh or less, or 5-mesh or less, may be incorporated into a food composition to induce the rodents to get the whiskers into their mouths. Once the rodents attempt to transport the materials by biting the whiskers with their teeth, or otherwise get the whiskers into their mouths, tiny fragments of the whiskers must be capable of lodging in the rodents' mouths. Generally, the compositions include at least 35% silica, with the balance being at least one other material selected from the group consisting of boric oxide, alumina, and lime. A preferred composition is one which contains between about 35–75% silica, 5–15% boric oxide, 4–24% alumina, 7–27% lime, and 1–7% magnesia by weight. Most preferably, the composition (by weight) of the whiskers is 55% silica, 10% boric oxide, 14% alumina, 17% lime, and 4% magnesia.

The whiskers of this invention may be used alone, by placing a shallow (2.0 inches or less in height) box with an open top portion, or other container which contains a plurality of the whiskers, wherein the whiskers are exposed for the rodents consideration, typically between about 25 grams and 100 grams for small rodent populations. This amount, or the number and density of the placing of such boxes may be varied in accordance with the desires of the user. The whiskers of this invention may even be spread out, or placed in piles near areas where the presence of rodents is either suspected or confirmed. Preferably, the whiskers of this invention either alone or in combination or intimate mixture with a foodstuff are contained in a square or rectangular shallow box constructed of thick paper, cardboard, or other similar material having, as but one non-limiting example, dimensions of say, about 6.0 inches×6.0 inches and a height of one inch. The top of the box is readily removed by virtue of perforations on the top panel of the box, the pattern of which is not critical but must only provide for exposure of at least 50% of the surface area of the box to the rodents.

In addition to the whiskers themselves, other rat poisons or attractants may be included or placed in close proximity with the whiskers in a given situation. Close proximity means within 1 inch. This includes other nesting materials such as hay, straw, cellulose, or any other material which rodents have observed to use in their nesting habit. Foodstuffs may be included, as well as organic rodenticide combinations, the use and composition of which are already known to those skilled in the art.

Although the present invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims which now follow.

I claim:

1. A rodenticide consisting of: a) a plurality of substantially linear, stiff glass whiskers having a diameter between 0.0025 and 0.100 inches, and having a length of between about 0.10 and 6.00 inches; and b) a foodstuff.

2. A rodenticide according to claim 1 wherein the diameter of said whiskers is between about 0.00375 inches and 0.00625 inches.

3. A rodenticide according to claim 1 wherein the diameter of said whiskers is between about 0.0045 inches and 0.0058 inches.

4. A rodenticide according to claim 1 wherein the length of said whiskers is between 0.500 inches and 2.500 inches.

5. A rodenticide according to claim 1 wherein said glass whiskers comprise at least about 35% silicon dioxide by weight.

6. A rodenticide according to claim 5 wherein said whiskers comprise at least about 1% magnesium oxide by weight.

7. A rodenticide according to claim 5 wherein said whiskers comprise at least about 3% calcium oxide by weight.

8. A rodenticide according to claim 5 wherein said whiskers comprise at least about 3% aluminum oxide by weight.

9. A rodenticide according to claim 5 wherein said whiskers comprise between about 35–75% silica, 5–15% boric oxide, 4–24% alumina, 7–27% lime, and 1–7% magnesia by weight.

10. A rodenticide according to claim 9 wherein said whiskers comprise about 55% silica, 10% boric oxide, 14% alumina, 17% lime, and 4% magnesia by weight.

11. A method of killing rodents which comprises the step of placing a rodenticide according to claim 1 in the vicinity of where rodents habituate.

12. A method of irritating the oral mucosa of rodents comprising the step of inducing a rodent to place a rodenticide according to claim 1 in its mouth and closing its jaw to the extent that at least one of said whiskers is caused to fracture or break, thus irritating said mucosa.

13. A method according to claim 12 wherein said inducing a rodent includes placing a material selected from the group consisting of: hay, straw, cellulose, newspaper, natural fibers and wood in close proximity to said whiskers.

14. A rodenticide consisting essentially of: a) a plurality of substantially linear, stiff glass whiskers having a diameter between 0.0025 and 0.100 inches, and having a length of between about 0.10 and 6.00 inches; and b) at least one material selected from the group consisting of: hay, straw, cellulose, newspaper, natural fibers, and wood.

15. A rodenticide according to claim 14 further containing a foodstuff.

16. A rodenticide according to claim 15 wherein said foodstuff is selected from the group consisting of: nuts, seeds, grain, sugars, dried fruits, vegetables, and dried meats.

17. A method of killing rodents which comprises the step of placing a rodenticide according to claim 14 in the vicinity of where rodents habituate.

* * * * *